United States Patent
Klausman et al.

(10) Patent No.: US 11,759,334 B2
(45) Date of Patent: Sep. 19, 2023

(54) HEIGHT AND LORDOSIS ADJUSTABLE SPACER

(71) Applicant: Astura Medical Inc., Irving, TX (US)

(72) Inventors: Keith Klausman, Irving, TX (US); Thomas Purcell, Irving, TX (US)

(73) Assignee: ASTURA MEDICAL INC., Irving, TX (US)

( * ) Notice: Subject to any disclaimer, the term of this patent is extended or adjusted under 35 U.S.C. 154(b) by 0 days.

(21) Appl. No.: 17/832,545

(22) Filed: Jun. 3, 2022

(65) Prior Publication Data

US 2022/0387190 A1 Dec. 8, 2022

Related U.S. Application Data

(60) Provisional application No. 63/196,314, filed on Jun. 3, 2021.

(51) Int. Cl.
*A61F 2/46* (2006.01)
*A61F 2/44* (2006.01)
*A61F 2/30* (2006.01)

(52) U.S. Cl.
CPC .......... *A61F 2/4611* (2013.01); *A61F 2/4455* (2013.01); *A61F 2002/30556* (2013.01); *A61F 2002/30579* (2013.01)

(58) Field of Classification Search
CPC .............................. A61F 2/4455–2/447; A61F 2250/0004–2250/001; A61F 2002/30556; A61F 2002/30579; B25B 23/0007; B25B 23/0035; B25B 23/0042; B25G 3/00; B25G 1/04; B25G 1/043; B25G 3/02
See application file for complete search history.

(56) References Cited

U.S. PATENT DOCUMENTS 11,185,421 B1 * 11/2021 Miller .................. A61F 2/4425
2018/0368983 A1    12/2018 Werner
2019/0021873 A1     1/2019 Dmuschewsky
(Continued)

OTHER PUBLICATIONS

International Search Report and Written Opinion in PCT Application No. PCT/US22/032268 dated Aug. 25, 2022.

*Primary Examiner* — Julianna N Harvey
*Assistant Examiner* — Angel Roberto Mora-Velazquez
(74) *Attorney, Agent, or Firm* — Michael R Shevlin

(57) ABSTRACT

An expandable interbody spacer that is delivered in the anterior approach with adjustable height and end plate angulation (lordosis). The expandable interbody spacer is configured to have an initial collapsed state having a first height suitable for being inserted into an intervertebral space defined by a pair of adjacent vertebrae, and an expanded state having a second height that is greater than the first height. The expandable interbody spacer may be expanded from the initial collapsed state to the expanded state in-situ. The expanded state increases the distance between the adjacent vertebrae and provides support to the adjacent vertebrae while bone fusion occurs and also provides rigid support between the adjacent vertebrae that withstands compressive forces. By inserting the expandable interbody spacer into the intervertebral space in the initial collapsed state, it is possible to perform the surgery percutaneously with minimal disruption to tissues surrounding the surgical site and intervening soft tissue structures.

5 Claims, 7 Drawing Sheets

(56) References Cited

U.S. PATENT DOCUMENTS

| | | |
|---|---|---|
| 2020/0015985 A1* | 1/2020 | Rogers .................. A61F 2/4455 |
| 2020/0281741 A1 | 9/2020 | Grotz |
| 2020/0390565 A1 | 12/2020 | Jimenez et al. |
| 2021/0085486 A1* | 3/2021 | Burrows-Ownbey ....................... A61F 2/4455 |
| 2021/0346174 A1* | 11/2021 | Flint .................... A61F 2/4455 |
| 2021/0378832 A1* | 12/2021 | Altarac ................. A61F 2/4455 |

* cited by examiner

HEIGHT AND LORDOSIS ADJUSTABLE SPACER

CROSS-REFERENCE TO RELATED APPLICATIONS

This application claims the benefit of U.S. Provisional Application No. 63/196,314 filed Jun. 3, 2021, which is incorporated herein by reference.

FIELD

The present invention relates generally to the field of surgery, and more specifically, to an expandable anterior interbody spacer having height and lordosis adjustment for placement in intervertebral space between adjacent vertebrae.

BACKGROUND

A spinal disc can become damaged as a result of degeneration, dysfunction, disease and/or trauma. Conservative treatment can include non-operative treatment through exercise and/or pain relievers to deal with the pain. In surgical treatments, interbody spacers may be used between adjacent vertebra, resulting in spinal fusion of the adjacent vertebra. Treatment options include disc removal and replacement using an interbody spacer, such as anterior cervical interbody fusion (ACIF), anterior lumbar interbody fusion (ALIF), direct lateral interbody fusion (DLIF) (also known as XLIF), posterior lumbar interbody fusion (PLIF), and transforaminal lumbar interbody fusion (TLIF).

The current standard of care for interbody fusion requires surgical removal of all or a portion of the intervertebral disc. After removal of the intervertebral disc, the interbody spacer is inserted into the intervertebral space to occupy the intervertebral space after the disc is removed. This requires that an opening sufficient to allow the interbody spacer must be created through surrounding tissue to permit the interbody spacer to be inserted into the intervertebral space.

In some cases, the interbody spacer may be required to change or correct the height and/or angle of the intervertebral space. This may be done by using an expandable interbody spacer that can be delivered in a collapsed state into the intervertebral space and then to an expanded state. Current expandable spacers delivered in an anterior approach do not provide the patient/surgeon with lordosis and/or height adjustability.

It would be desirable to develop an expandable interbody spacer that can be inserted into the intervertebral space using an anterior approach that provides full adjustability of height and lordosis.

SUMMARY

Disclosed is an expandable interbody spacer that is delivered in the anterior approach with adjustable height and end plate angulation (lordosis). The expandable interbody spacer is configured to have an initial collapsed state having a first height suitable for being inserted into an intervertebral space defined by a pair of adjacent vertebrae, and an expanded state having a second height that is greater than the first height. The expandable interbody spacer may be expanded from the initial collapsed state to the expanded state in-situ. The expanded state increases the distance between the adjacent vertebrae and provides support to the adjacent vertebrae while bone fusion occurs and also provides rigid support between the adjacent vertebrae that withstands compressive forces. By inserting the expandable interbody spacer into the intervertebral space in the initial collapsed state, it is possible to perform the surgery percutaneously with minimal disruption to tissues surrounding the surgical site and intervening soft tissue structures.

7 is a perspective view of the distal portion of the inserter instrument.

Figure 8:
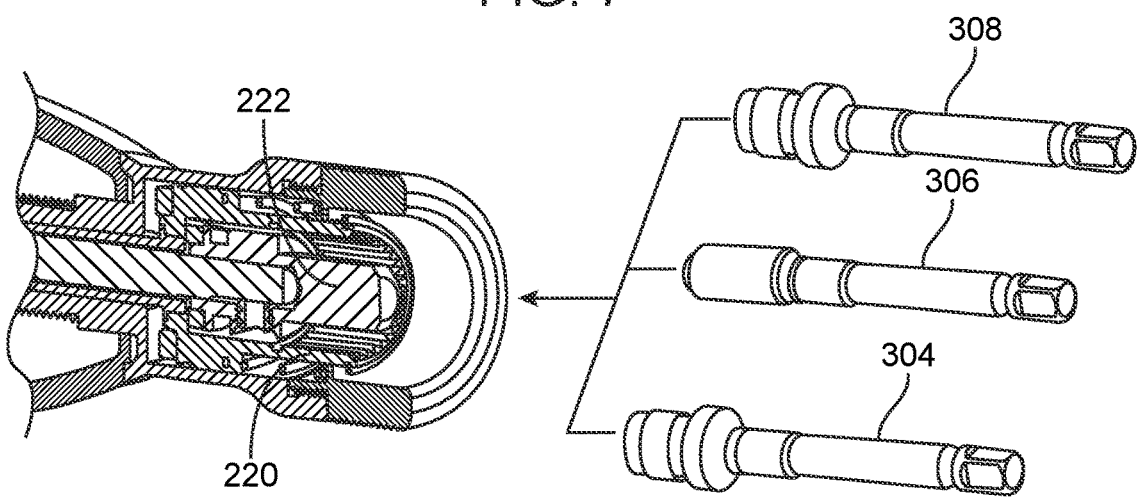

FIG. 8 is a cross-sectional view showing proximal end of the inserter instrument.

Figure 9:
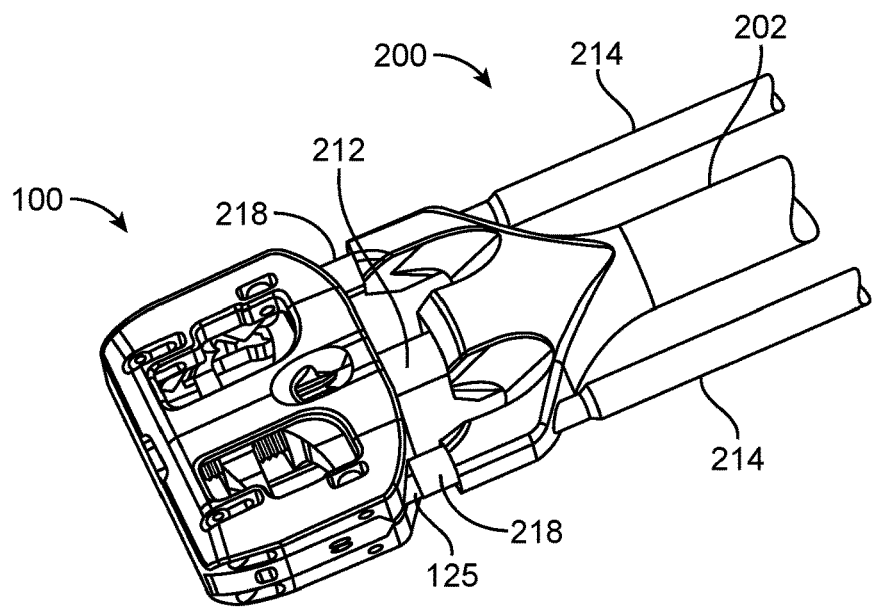

FIG. 9 is a perspective view of the distal portion of the inserter instrument coupled with the expandable interbody spacer.

Figure 10:
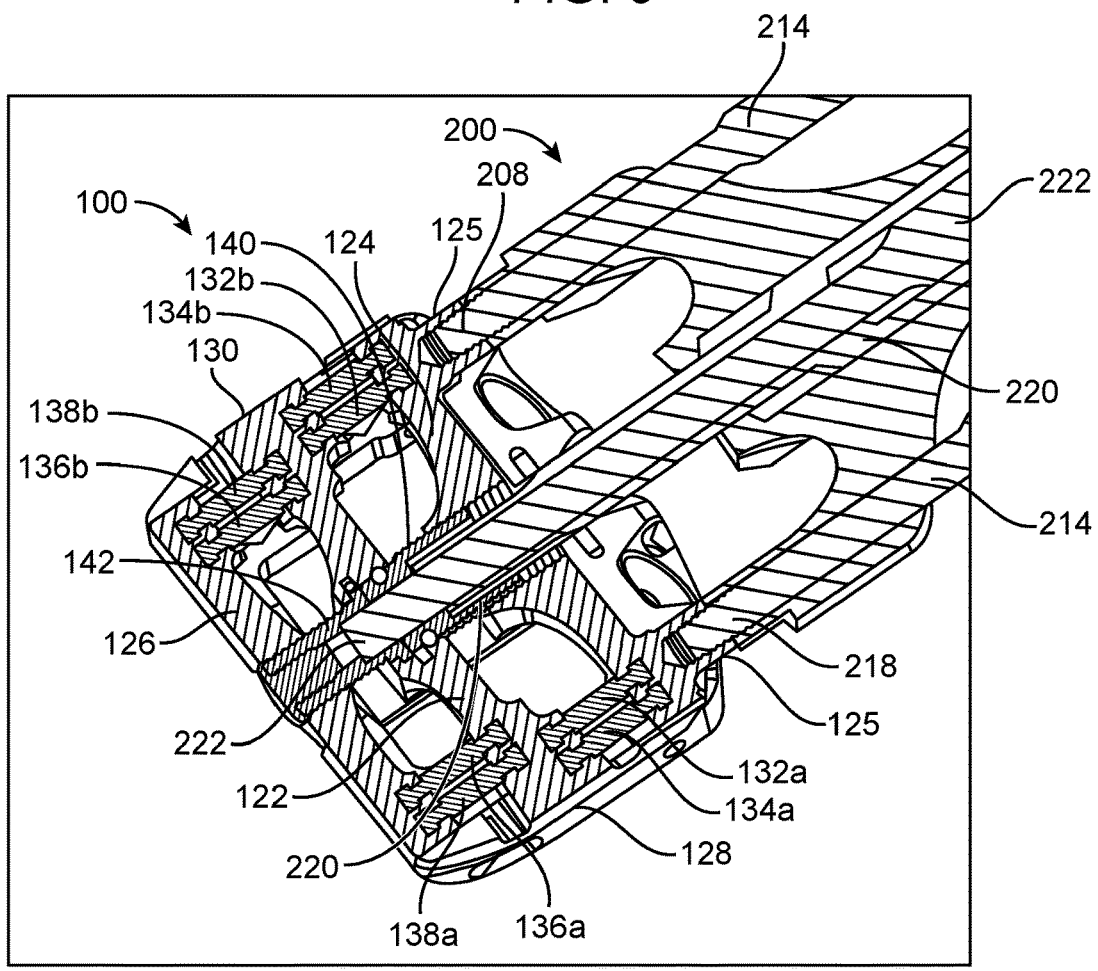

FIG. 10 is a sectional view of FIG. 9 showing the expandable interbody spacer coupled to the distal end of the inserter instrument.

Figure 11:
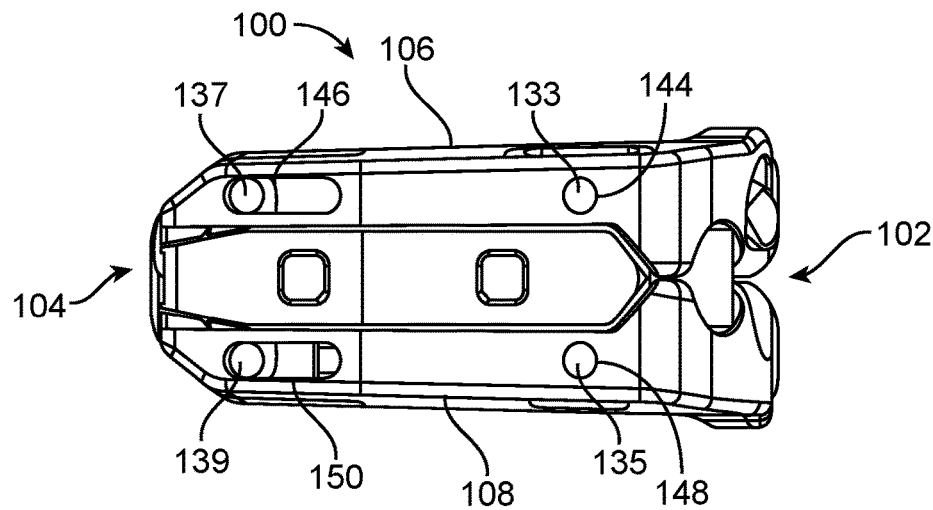

FIG. 11 is a side view of the expandable interbody spacer 100 in a collapsed configuration for delivery.

Figure 12:
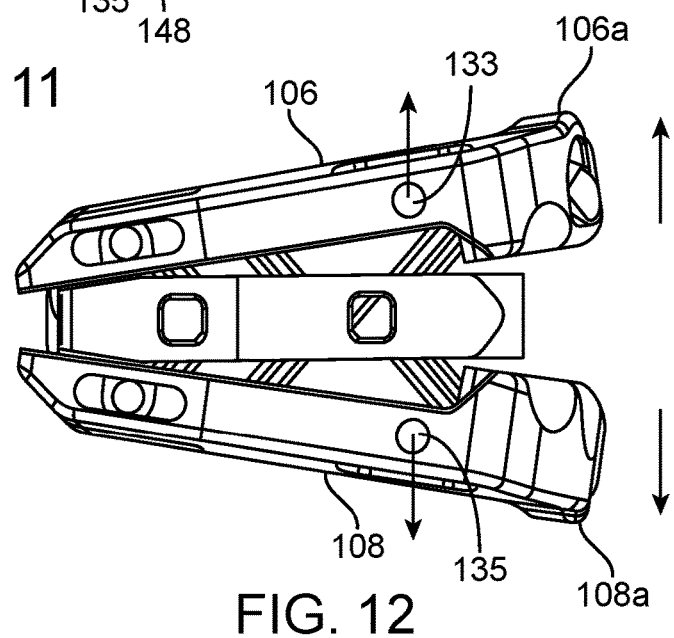

FIG. 12 shows one embodiment of the expandable interbody spacer in which only the proximal end upper and lower end plates are expanded to treat lordosis.

Figure 13:
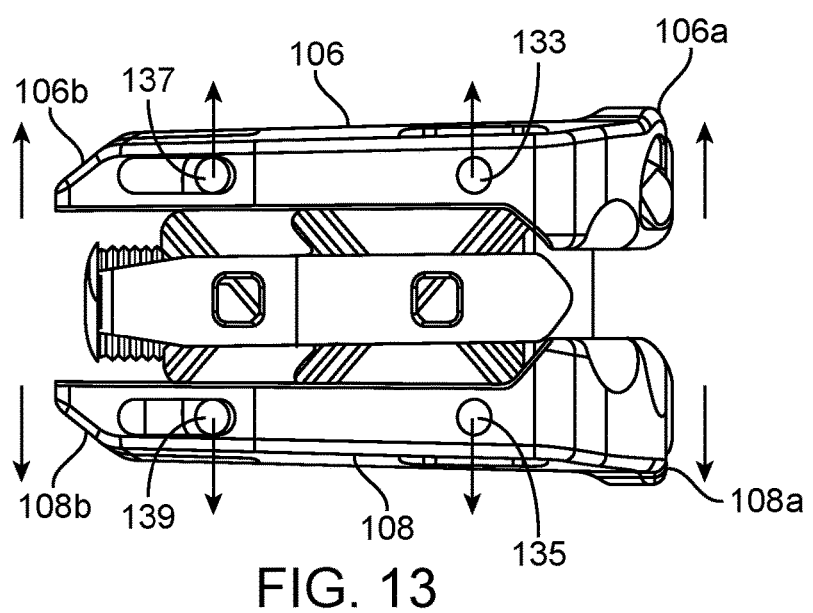

FIG. 13 shows one embodiment of the expandable interbody spacer in which both the proximal end upper and lower end plates are expanded to increase the height of the expandable interbody spacer.

Figure 14:
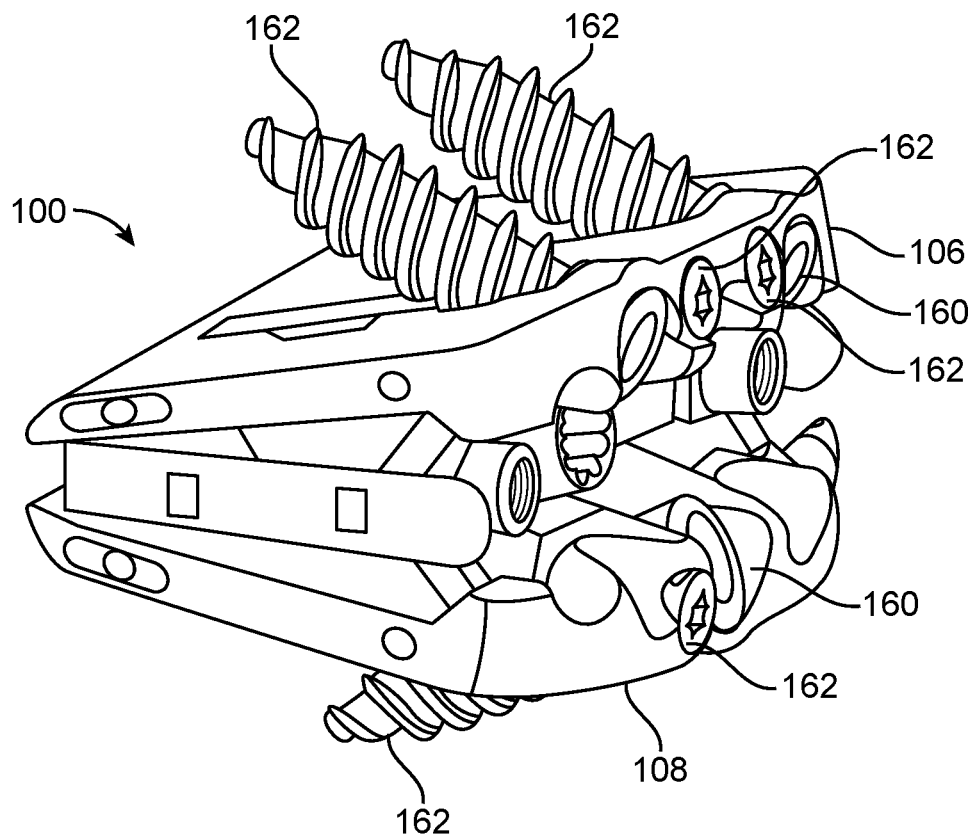

FIG. 14 shows one embodiment of an expandable interbody spacer that includes screw holes sized to receive bone screws to anchor the expandable interbody spacer 100 between two vertebrae.

Figure 15:
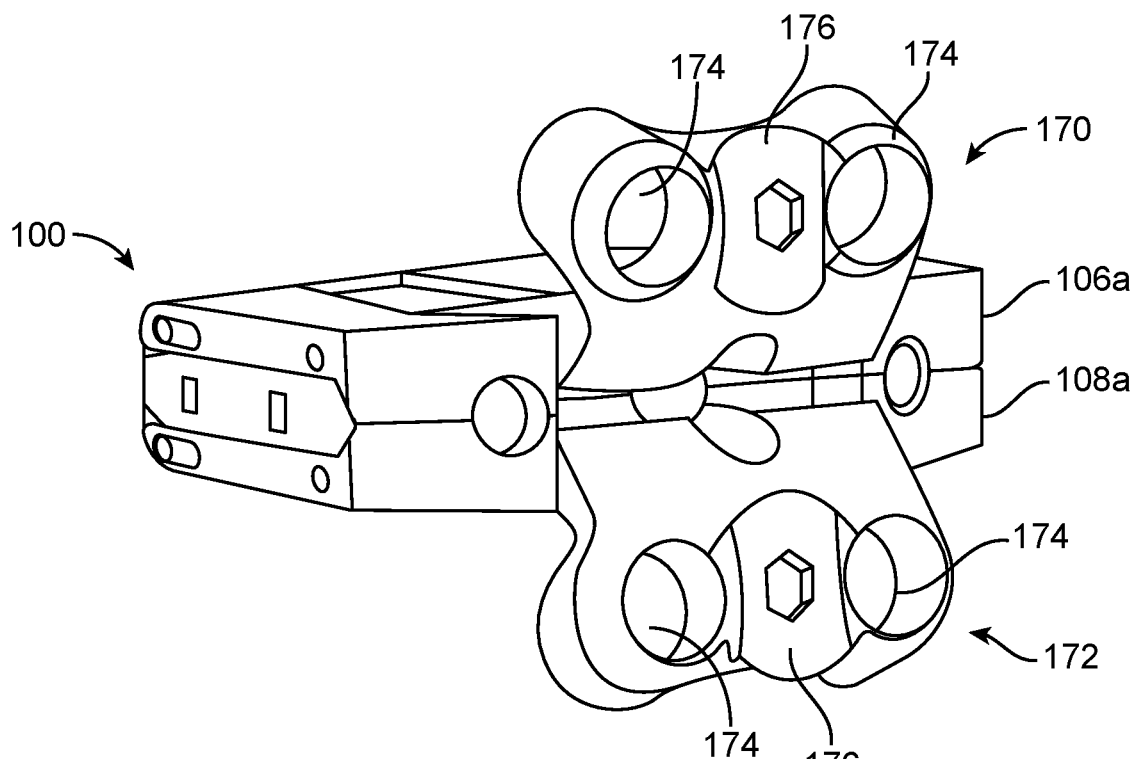

FIG. 15 shows one embodiment of an expandable interbody spacer that includes upper lower attachment plates coupled to the proximal end of the upper and lower end plates.

DETAILED DESCRIPTION

The expandable interbody spacer disclosed is designed for height and lordosis adjustability in interbody fusion, such as anterior lumbar interbody fusion (ALIF) that is delivered in the anterior approach. The expandable interbody spacer includes a collapsed state with minimal dimensions for insertion between adjacent vertebrae and an expanded state once in place between adjacent vertebrae. The end plates may be textured to promote bony integration.

Figure 1:
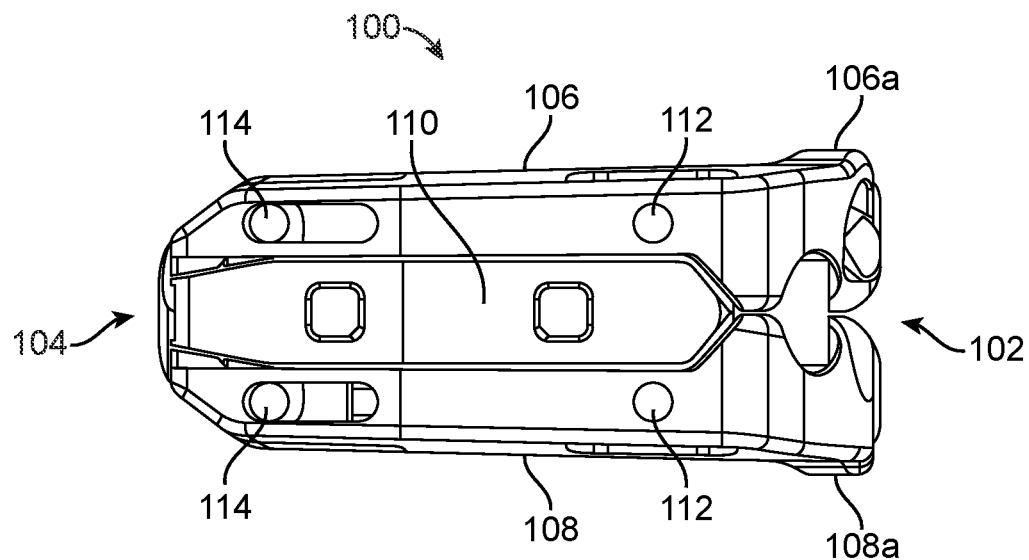
FIG. 1 is a side view of an expandable interbody spacer in a collapsed state for introduction into disc space.
Figure 2:
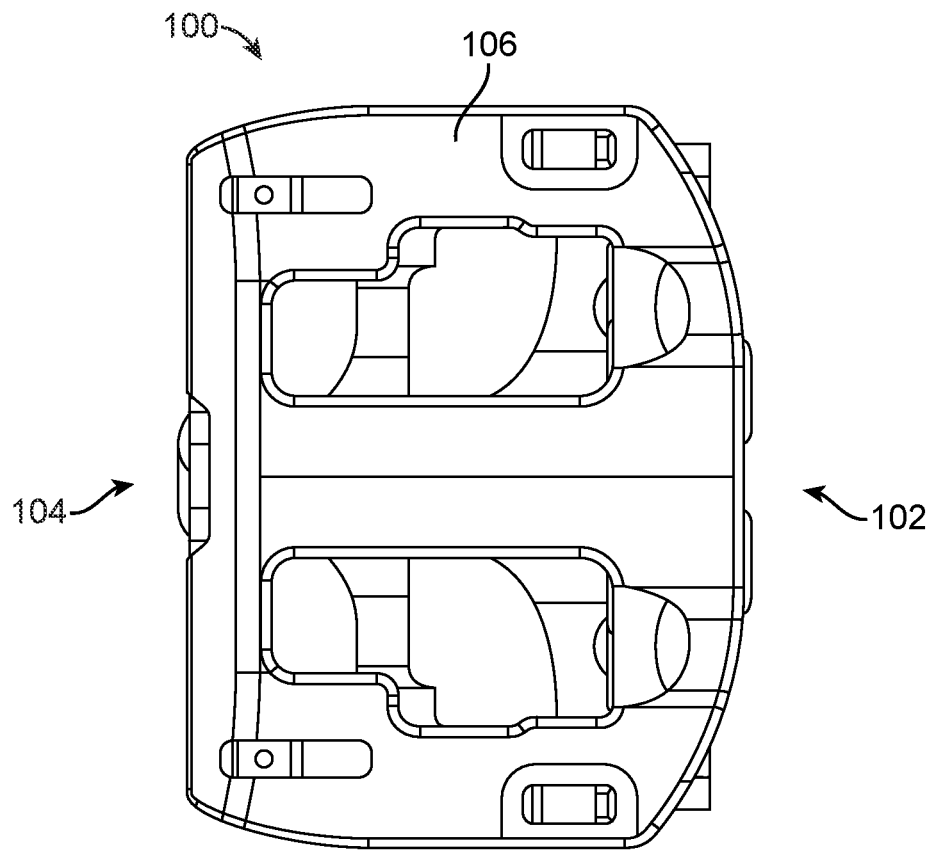
FIG. 2 is a top view showing the expandable interbody spacer of FIG. 1.

FIGS. 1 and 2 are a side view and a top view showing one embodiment of an expandable interbody spacer 100 having a proximal end 102, a distal end 104, an upper end plate 106, a lower end plate 108 and a central drive assembly 110 with a proximal rotatable drive assembly 112 and a distal rotatably drive assembly 114. The proximal rotatable drive assembly 112 is rotatably coupled to a proximal portion 106a, 108a of the upper and lower end plates 106, 108 and the distal rotatably drive assembly 114 is rotatably coupled to a distal portion 106b, 108b of the upper and lower end plates 106, 108.

In one embodiment to treat anterior-to-posterior lordosis, the proximal rotatable drive assembly 112 is configured to push the proximal ends 106a, 108a away from each other to expand, forming an anterior 102 to posterior 104 angle for the implant 100. The anterior 102 to posterior 104 angle for the implant 100 is adjustable and may be increased or decreased using the proximal rotatable drive assembly 112.

To increase the height of the implant, the proximal and distal rotatable drive assemblies 112, 114 are configured to push the proximal ends 106a, 108a and distal ends 106b, 108b away from each other to expand the upper and lower end plates 106, 108 to increase the height of the expandable interbody spacer 100. The height of the implant 100 is adjustable and may be increased or decreased using the proximal and distal rotatable drive assemblies 112, 114.

Figure 3:
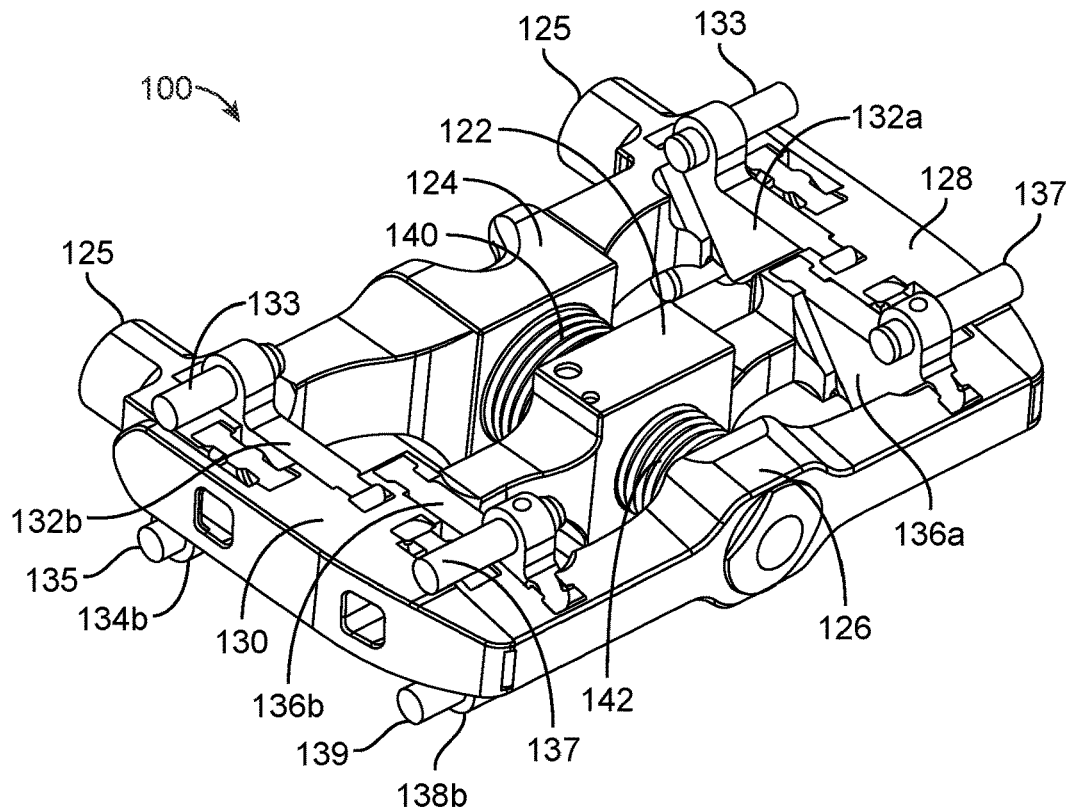
FIG. 3 is a perspective view showing one embodiment of the drive assembly.

FIG. 3 is a perspective view showing one embodiment of the drive assembly 110 having a center cross member 122, a proximal cross member 124, a distal cross member 126, left frame rail 128, a right frame rail 130, left and right proximal upper wedge-shaped T-rails 132a, 132b, left and right proximal lower wedge-shaped T-rails 134a, 134b, left and right distal upper wedge-shaped T-rails 136a, 136b, left and right distal lower wedge-shaped T-rails 138a, 138b, a proximal rotatable drive member 140 and a distal rotatable drive member 142. The left and right frame rails 128, 130 include proximal slots 144 configured to slidingly receive the proximal cross member 124, and distal slots 146 configured to slidingly receive the distal cross member 126. The proximal and distal rotatable drive members 140, 142 include external threads that engage internal threads of the proximal and distal cross members 124, 126. The proximal cross member 124 further includes proximal protrusions 125 having threaded holes.

The center cross member 122 and the proximal cross member 124 include opposing ramped portions configured to slidingly engage the proximal upper and lower wedge-shaped T-rails 132a, 132b, 134a, 134b. The proximal upper and lower wedge-shaped T-rails 132a, 132b, 134a, 134b also include upper and proximal lower engagement pins 133,135 configured to rotatably engage proximal pin engagement holes 144, 148 in the upper and lower end plates 106, 108.

The center cross member 122 and the distal cross member 126 include opposing ramped portions configured to slidingly engage the distal upper and lower wedge-shaped T-rails 136a, 135b, 138a, 138b. The distal upper and distal lower wedge-shaped T-rails 136a, 135b, 138a, 138b also include upper and distal lower engagement pins 137, 139 configured to slidingly engage distal pin engagement slots 146, 150 in the upper and lower end plates 106, 108.

The proximal rotatable drive member 140 is coupled to the center cross member 122 and the proximal cross member 124, and the distal rotatable drive member 142 is coupled to the center cross member 122 and the distal cross member 126. The distal rotatable drive member 142 may be smaller than the proximal rotatable drive member 140 to allow for independent adjustability via an inserter instrument 200 (see FIG. 6).

Figure 4:
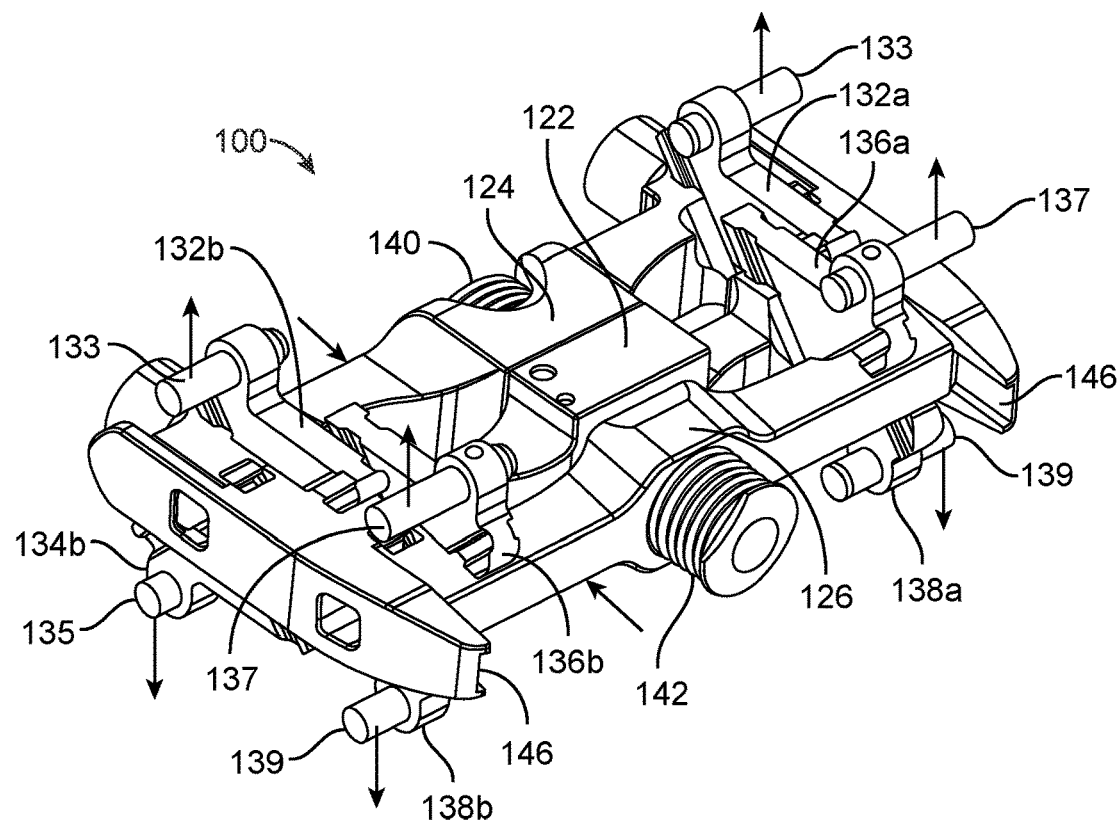
FIG. 4 is a perspective view showing the operation of the drive assembly of FIG. 3.

FIG. 4 shows the operation of the drive assembly 110. The external threads of the proximal rotatable drive member 140 engage a threaded opening in the proximal cross member 124. When the proximal rotatable drive member 140 is rotated in a first direction the proximal cross member 124 is pulled toward the center cross member 122. As the proximal cross member 124 moves toward the center cross member 122, the opposing ramps engage the proximal upper and lower wedge-shaped T-rails 132, 134 to push them outward from the upper and lower T-rail slots. This increases the distance between the upper and lower end plate engagement pins 133, 135. This also increases the distance between the proximal ends 106a, 108a of the upper and lower end plates 106, 108 (see FIG. 12). When the proximal rotatable drive member 140 is rotated in a second direction, the proximal cross member 124 moves away the center cross member 122. As the proximal cross member 124 moves away the center cross member 122, the proximal upper and lower wedge-shaped T-rails 132, 134 move inward or downward into the upper and lower T-rail slots. This decreases the distance between the upper and lower end plate engagement pins 133, 135. This also decreases the distance between the proximal ends 106a, 108a of the upper and lower end plates 106, 108.

The external threads of the distal rotatable drive member 142 engage a threaded opening in the distal cross member 126. When the distal rotatable drive member 142 is rotated in a first direction the distal cross member 126 is pulled toward the center cross member 122. As the distal cross member 126 moves toward the center cross member 122, the opposing ramps engage the distal upper and lower wedge-shaped T-rails 136, 138 to push them outward from the upper and lower T-rail slots. This increases the distance between the upper and lower end plate engagement pins 137, 139. This also increases the distance between the distal ends 106b, 108b of the upper and lower end plates 106, 108 (see FIG. 13). When the distal rotatable drive member 142 is rotated in a second direction, the distal cross member 126 moves away the center cross member 122. As the distal cross member 126 moves away the center cross member 122, the distal upper and lower wedge-shaped T-rails 136, 138 move inward into the upper and lower T-rail slots. This decreases the distance between the upper and lower end plate engagement pins 137, 139. This also decreases the distance between the distal ends 106b, 108b of the upper and lower end plates 106, 108.

Figure 5:
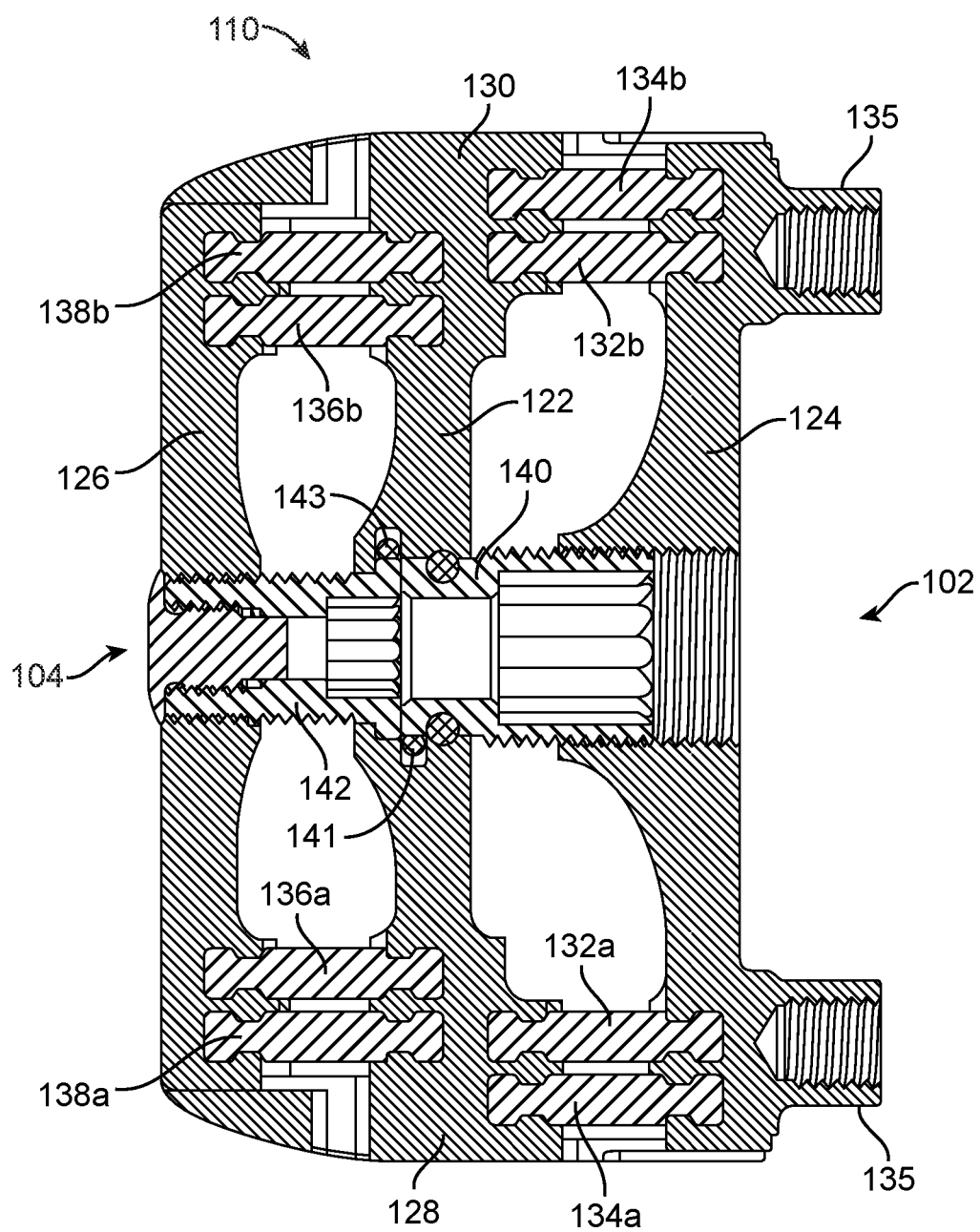
FIG. 5 is a sectional view of the drive assembly showing the relationship of the components.

FIG. 5 is a sectional view of the drive assembly 110 showing the relationship of the components, including the center cross member 122, a proximal cross member 124, a distal cross member 126, left frame rail 128, a right frame rail 130, proximal upper wedge-shaped T-rails 132a, 132b, proximal lower wedge-shaped T-rails 134a, 134b, distal upper wedge-shaped T-rails 136a, 136b, distal lower wedge-shaped T-rails 138a, 138b, a proximal rotatable drive member 140 and a distal rotatable drive member 142. There are also two nitinol wires 141, 143 configured to contact the proximal rotatable drive member 140 and the distal rotatable drive member 142 within the spacer to resist rotation of the proximal and distal rotatable drive members 140, 142 once the inserter instrument 200 has been removed.

While a rotatable drive member is shown, the drive mechanism can be any mechanism capable of moving the center cross member, proximal cross member and distal cross member toward or away from each other to expand or collapse the expandable interbody spacer 100.

Figure 6:
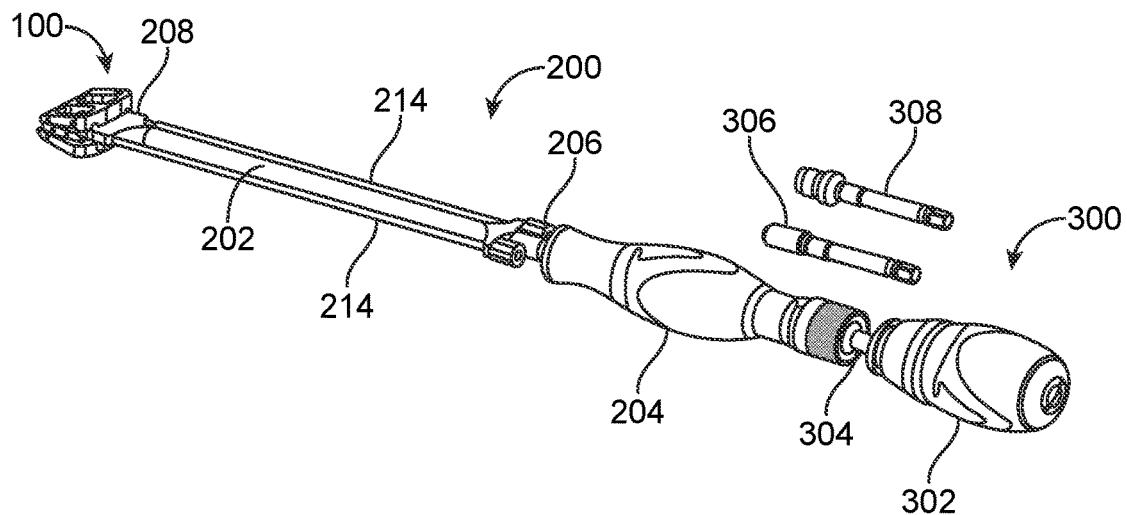
FIG. 6 is a perspective view showing one embodiment of an inserter instrument configured to couple with the expandable interbody spacer.

FIG. 6 is a perspective view showing one embodiment of an inserter instrument 200 configured to couple with the expandable interbody spacer 100 for delivery and expansion of the expandable interbody spacer 100 after delivery. The inserter instrument includes body 202 having handle 204 coupled to a proximal end 206, a distal end 208, and a cannula 210 sized to slidably receive a driver shaft 212. The inserter instrument 200 further includes one or more threaded rods 214 positioned adjacent to the body 202 with a proximal handle 216 and a distal end 218 configured to couple with the expandable interbody spacer 100.

The proximal end of the driver shaft 212 is configured to couple with a modular quick connect driver 300 having a handle 302 configured to hold multiple quick connect drivers 304, 306, 308. A distal end of the quick connect drivers 304, 306, 308 are configured to engage the proximal end of the driver shaft 212.

Figure 7:
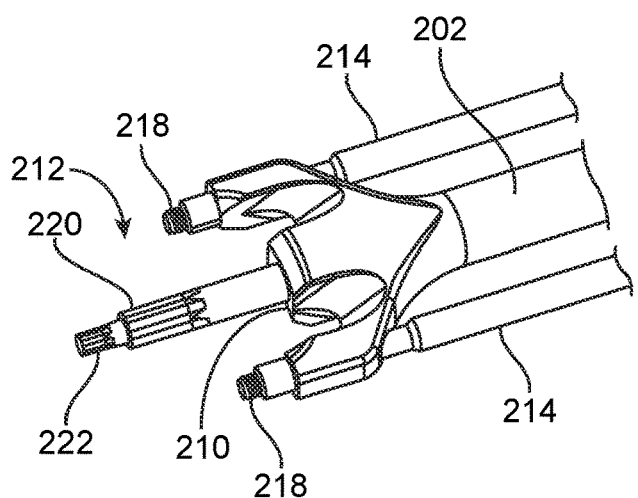

FIG. 7 is a perspective view of the distal portion of the inserter instrument 200 showing the modular quick connect driver 212 extending distally from the cannula 210 of the body 202 and the distal end 218 of the threaded rods 214 configured to couple with the expandable interbody spacer 100. The driver shaft 212 includes an outer driver shaft 220 having a distal end configure to engage the proximal rotatable drive member 140 and an inner drive shaft 222 having a distal end configured to engage the distal rotatable drive member 142. The outer and inner driver shafts 220, 222 may be operated separately or together.

FIG. 8 is a cross-sectional view showing proximal end of the inserter instrument 200 and the proximal end of the outer and inner driver shafts 220, 222. The outer and inner driver shafts 220, 222 may be operated separately or together depending on the quick connect driver 304, 306, 308 that is used. For example, a first quick connect driver 304 is configured to couple with the outer drive shaft 220 to rotate the proximal rotatable drive member 140 to expand or collapse the proximal end of the expandable interbody spacer 100. The second quick connect driver 306 is configured to couple with the inner drive shaft 222 to rotate the distal rotatable drive member 142 to expand or collapse the distal end of the expandable interbody spacer 100. The third quick connect driver 308 is configured to couple with both the outer and inner drive shafts 220, 222 to rotate both the proximal and distal rotatable drive members 140, 142 to expand or collapse the proximal and distal ends of the expandable interbody spacer 100.

FIG. 9 is a perspective view of the distal portion of the inserter instrument 200 coupled with the expandable interbody spacer 100.

FIG. 10 is a sectional view of FIG. 9 showing the expandable interbody spacer 100 coupled to the distal end of the inserter instrument 100. The distal end 218 of the threaded rods 214 are coupled to the threaded holes of the proximal protrusion 125. The outer drive shaft 220 is coupled to the proximal rotatable drive member 140 and the inner drive shaft 222 is coupled to the proximal rotatable drive member 140.

FIG. 11 is a side view of the expandable interbody spacer 100 in a collapsed configuration for delivery. The upper end plate 106 includes proximal engagement pin holes 144 and distal engagement pin slots 146. The proximal engagement pin holes 144 being configured to rotatably couple to the proximal upper engagement pins 133 and the distal engagement pin slots 146 being configured to slidingly couple with the distal upper engagement pins 137. The lower end plate 108 includes proximal engagement pin holes 148 and distal engagement pin slots 150. The proximal engagement pin holes 148 being configured to rotatably couple to the proximal lower engagement pins 135 and the distal engagement pin slots 150 being configured to slidingly couple with the distal lower engagement pins 139.

FIG. 12 shows one embodiment of the expandable interbody spacer 100 in which only the proximal end upper and lower end plates 106, 108 are expanded to treat lordosis. An inserter instrument is coupled to the proximal end of the expandable interbody spacer 100 (see FIG. 6) to actuate the proximal rotatable drive member 140 so the proximal cross member 124 moves toward the center cross member 122 and the upper and proximal lower wedge-shaped T-rails 132, 134 are pushed outward expanding the proximal ends 106a, 108a of the upper and lower end plates 106, 108 from a first collapsed position to a second expanded position. The expansion the proximal ends 106a, 108a increase the height of the proximal end 102 so that the upper and lower end plates 106, 108 are angled to treat lordosis.

FIG. 13 shows one embodiment of the expandable interbody spacer 100 in which both the proximal end upper and lower end plates 106, 108 are expanded to increase the height of the expandable interbody spacer 100. An inserter instrument is coupled to the proximal end of the expandable interbody spacer 100 (see FIG. 6) to actuate both the proximal and distal rotatable drive members 140, 142 so the proximal distal cross members 124, 126 move toward the center cross member 122. As the proximal cross member 124 moves toward the center cross member 122 and the upper and proximal lower wedge-shaped T-rails 132, 134 are pushed outward expanding the proximal ends 106a, 108a of the upper and lower end plates 106, 108 from a first collapsed position to a second expanded position. As the distal cross member 126 moves toward the center cross member 122 and the upper and distal lower wedge-shaped T-rails 136, 138 are pushed outward expanding the proximal distal ends 106b, 108b of the upper and lower end plates 106, 108 from a first collapsed position to a second expanded position (see FIG. 4). Expanding the proximal ends 106a, 108a and distal ends 106b, 108b away from each other from a first position to a second position, expands upper and lower end plates 106, 108 so they are parallel. The expansion of the upper and lower end plates 106, 108 increases the height of the expandable interbody spacer 100.

FIG. 14 shows one embodiment of an expandable interbody spacer 100 that includes two more screw holes 160 in the upper and lower end plates 106, 108 sized to receive bone screws 162 configured to anchor the expandable interbody spacer 100 between two vertebrae of the spine. The expandable interbody spacer 100 may also include bone screw locking features 164 to prevent the bone screw 162 from backing out of the screw holes 160.

FIG. 15 shows one embodiment of an expandable interbody spacer 100 that includes an upper attachment plate 170 coupled to the proximal end 106a of the upper end plate 106 and a lower attachment plate 172 coupled to the proximal end 108a of the upper end plate 108. The upper and lower attachment plates 170, 172 include two more screw holes 174 sized to receive bone screws configured to anchor the expandable interbody spacer 100 between two vertebrae of the spine. The expandable interbody spacer 100 may also include bone screw locking features 176 to prevent the bone screw from backing out of the screw holes 174.

The upper and lower end plates may include surface features or treatment configured to promote bone growth that engage the bone. For example, the surface may be a textured surface or roughened surface to promote bone integration or the surface may use a coating or be chemically etched to form a porous or roughened surface. In some embodiments the surface may include teeth. Each of the upper and lower end plates may use the same surface feature or different surface feature.

The expandable interbody spacer 100 components may be fabricated from any biocompatible material suitable for implantation in the human spine, such as metal including, but not limited to, titanium and its alloys, stainless steel, surgical grade plastics, plastic composites, ceramics, bone, or other suitable materials. In some embodiments, surfaces on the components may be formed of a porous material that participates in the growth of bone with the adjacent vertebral bodies. In some embodiments, the components may include a roughened surface that is coated with a porous material, such as a titanium coating, or the material is chemically etched to form pores that participate in the growth of bone with the adjacent vertebra. In some embodiments, only portions of the components be formed of a porous material, coated with a porous material, or chemically etched to form a porous surface, such as the upper and lower surfaces 144 that contact the adjacent vertebra are roughened or porous.

In operation, the expandable interbody spacer 100 may be inserted into the intervertebral disc space between two vertebrae using an insertion tool. In some cases, the disc space may include a degenerated disc or other disorder that may require a partial or complete discectomy prior to insertion of the expandable interbody spacer 100. The deployment tool may engage with the proximal end of the expandable interbody spacer 100. As the deployment tool applies the rotational force, the expandable interbody spacer 100 gradually expands as described above.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. An expandable interbody spacer for placement between adjacent vertebrae comprising:
    an upper endplate having a proximal end and a distal end;
    a lower endplate having a proximal end and a distal end;
    a proximal rotatable drive assembly coupled to the proximal ends of the upper and lower endplates, the proximal rotatable drive assembly being configured to push the proximal ends of the upper and lower endplates away from each other to expand a proximal end of the expandable interbody spacer;
    a distal rotatable drive assembly coupled to the distal ends of the upper and lower endplates and configured to push the distal ends of the upper and lower endplates away from each other to expand a distal end of the expandable interbody spacer;
    an inserter instrument configured to couple with the expandable interbody spacer, the inserter instrument having a modular quick connect driver coupled to a proximal end of a driver shaft, the driver shaft includes an outer drive shaft coupled to the proximal rotatable drive assembly and an inner drive shaft coupled to the distal rotatable drive assembly, the modular quick connect driver configured to operate the outer drive shaft and the inner drive shaft separately or together;
    wherein the modular quick connect driver includes:
        a first quick connect driver configured to couple with the outer drive shaft to rotate the proximal rotatable drive assembly to expand or collapse the proximal end of the expandable interbody spacer;
        a second quick connect driver configured to couple with the inner drive shaft to rotate the distal rotatable drive assembly to expand or collapse the distal end of the expandable interbody spacer; and
        a third quick connect driver configured to couple with both the outer and inner drive shafts to rotate both the proximal and distal rotatable drive assemblies to expand or collapse the proximal and distal ends of the expandable interbody spacer.

2. The expandable interbody spacer of claim 1, wherein pushing the proximal ends of the upper and lower endplates away from each other forms an anterior to posterior angle between the upper and lower endplates to treat anterior-to-posterior lordosis.

3. The expandable interbody spacer of claim 2, wherein the anterior to posterior angle is adjustable and may be increased or decreased using the proximal rotatable drive assembly.

4. The expandable interbody spacer of claim 1, wherein pushing the proximal ends and distal ends of the upper and lower endplates away from each other increases a height of the expandable interbody spacer.

5. The expandable interbody spacer of claim 4, wherein the height of the expandable interbody spacer is adjustable and may be increased or decreased using the proximal and distal rotatable drive assemblies.

\* \* \* \* \*